United States Patent
Delahaye et al.

(10) Patent No.: US 11,995,661 B2
(45) Date of Patent: May 28, 2024

(54) WATER MANAGEMENT FOR AN INDUSTRIAL SITE

(71) Applicant: Total SE, Courbevoie (FR)

(72) Inventors: Bruno Delahaye, Egly (FR); Frédéric Perie, Billère (FR); Matthieu Jacob, Cescau (FR); Elsa Maurice, Paris (FR); Jean-Baptiste Bayart, Lausanne (CH)

(73) Assignee: Total SE, Courbevoie (FR)

( * ) Notice: Subject to any disclaimer, the term of this patent is extended or adjusted under 35 U.S.C. 154(b) by 359 days.

(21) Appl. No.: 17/296,831

(22) PCT Filed: Dec. 11, 2019

(86) PCT No.: PCT/EP2019/084767
§ 371 (c)(1),
(2) Date: May 25, 2021

(87) PCT Pub. No.: WO2020/120639
PCT Pub. Date: Jun. 18, 2020

(65) Prior Publication Data
US 2021/0398140 A1 Dec. 23, 2021

(30) Foreign Application Priority Data
Dec. 13, 2018 (EP) .................................. 18306686

(51) Int. Cl.
*G06Q 30/00* (2023.01)
*C02F 1/00* (2023.01)
(Continued)

(52) U.S. Cl.
CPC .......... *G06Q 30/018* (2013.01); *C02F 1/008* (2013.01); *G01N 33/18* (2013.01); *G06F 16/26* (2019.01);
(Continued)

(58) Field of Classification Search
CPC ......... G01N 33/18; G06F 16/26; C02F 1/008; G06Q 10/0635; G06Q 10/067; G06T 11/206
See application file for complete search history.

(56) References Cited

U.S. PATENT DOCUMENTS

2007/0219728 A1* 9/2007 Papageorgiou ....... G06T 11/206
702/23
2011/0141117 A1* 6/2011 Barba .................... G06Q 10/06
345/440
(Continued)

FOREIGN PATENT DOCUMENTS

EP           2348468 A1    7/2011
WO       2020/120639 A1    6/2020
WO    WO-2020120639 A1 *  6/2020  .............. C02F 1/008

OTHER PUBLICATIONS

International Search Report and The Written Opinion for International Application No. PCT/EP2019/084767, entitled "Water Management for an Industrial Site," dated Feb. 5, 2020, 7 pages.

*Primary Examiner* — Todd Buttram
(74) *Attorney, Agent, or Firm* — Hamilton, Brook, Smith & Reynolds, P.C.

(57) ABSTRACT

The invention notably relates to a computer-implemented method of water management for an industrial site, the method comprising collecting, via user-interaction, data related to one or more exploitation scenarios of the industrial site, for each respective exploitation scenario, computing, automatically by a computer system and based on the collected data, for each indicator of a plurality of indicators, a respective indicator value, the plurality of indicators comprising a first group of one or more water risk assessment indicators and a second group of one or more environmental footprint indicators, and displaying, simultaneously on a display of the computer system, a plurality of (Continued)

graphical representations including for the indicator value of each indicator of the first group and the second group, a respective graphical representation. The invention improves water management for an industrial site.

18 Claims, 7 Drawing Sheets

(51) Int. Cl.
| | |
|---|---|
| *G01N 33/18* | (2006.01) |
| *G06F 16/26* | (2019.01) |
| *G06Q 10/06* | (2023.01) |
| *G06Q 10/0635* | (2023.01) |
| *G06Q 10/067* | (2023.01) |
| *G06Q 30/018* | (2023.01) |
| *G06T 11/20* | (2006.01) |
| *C02F 103/10* | (2006.01) |
| *G06Q 10/30* | (2023.01) |
| *G06Q 50/06* | (2012.01) |

(52) U.S. Cl.
CPC ....... *G06Q 10/0635* (2013.01); *G06Q 10/067* (2013.01); *G06T 11/206* (2013.01); *C02F 2103/10* (2013.01); *C02F 2209/006* (2013.01); *C02F 2209/08* (2013.01); *G06Q 10/30* (2013.01); *G06Q 50/06* (2013.01)

(56) References Cited

U.S. PATENT DOCUMENTS

2015/0177917 A1* 6/2015 Hoekstra ................ G06Q 10/10
715/771
2021/0398140 A1* 12/2021 Delahaye ............. G06Q 10/067

* cited by examiner

FIG. 3

Sludge management (all type of liquid waste)

| | User comments | Guidelines | Unit | Default data | User data | Data used |
|---|---|---|---|---|---|---|
| Incineration | | | | | | |
| Quantity of wet matter | | Mention the quantity of sludge sent to incineration | kg/yr | | | 0.00 |
| Dry matter content | | Mention the dry matter content | % | | | 0% |
| Fossil carbon content | | Mention the fossil carbon content of the sludge (default data proposed: 100% of the carbon is from a fossil origin) | kg fossil C/kg dry matter | 1 | | 1.00 |
| Lower Heating Value (dry matter) | | Mention the lower heating value of the sludge (dry matter). Example of Lower Heating Value: Diesel: 43,4 MJ/kg; Crude Oil: 45,8 MJ/kg; Lignite hard: 17,8MJ/kg; soft Wood: 10,8 MJ/kg | MJ/kg dry matter | | | 0.00 |
| Transportation distance | | Mention the transportation distance between the site and the incineration location | km | | | 0.00 |

30

32', 33', 31', 110'

| | | Baseline | Water Use scenario 1 | Water Use scenario 2 | Water Use scenario 3 | Unit |
|---|---|---|---|---|---|---|
| Water Risk Assesss. | Physical / water stress | 0.00 | 0.00 | 0.00 | 0.00 | *index* |
| | Physical / water quality | 0.00 | 0.00 | 0.00 | 0.00 | *index* |
| | Regulatory | 0.00 | 0.00 | 0.00 | 0.00 | *index* |
| | Reputational | 0.00 | 0.00 | 0.00 | 0.00 | *index* |
| | Technological risk | 0.00 | 0.00 | 0.00 | 0.00 | *index* |
| Enviro. Footprint | Carbon footprint | 0 | 0 | 0 | 0 | kg CO2-eq/yr |
| | Freshwater withdrawal | 0 | 0 | 0 | 0 | m3/yr |
| | Water scarcity footprint | 0 | 0 | 0 | 0 | m3-eq/yr |
| | COD | 0 | 0 | 0 | 0 | kg/yr |
| | Freshwater ecotoxicity | 0 | 0 | 0 | 0 | CTUe/yr |

FIG. 4

WATER MANAGEMENT FOR AN INDUSTRIAL SITE

This application is the U.S. National Stage of International Application No. PCT/EP2019/084767, filed Dec. 11, 2019, which designates the U.S., published in English, and claims priority under 35 U.S.C. § 119 or 365(c) to EP Application No. 18306686.9, filed Dec. 13, 2018. The entire teachings of the above applications are incorporated herein by reference.

TECHNICAL FIELD

The disclosure relates to the field of water management for an industrial site.

BACKGROUND

Decisions to invest in water treatment technologies have always been motivated by the analysis of their performance. However, other factors could also justify the choice of water management scenarios (reduction, reuse, recycling and use). Methods based on existing decision support tools are often restrictive, as only an incomplete set of indicators is taken into account. These methods are not flexible enough to evaluate the different water management scenarios in a systematic way. This presents the risk of disregarding indicators of interest.

There is thus a need to improve water management for an industrial site.

SUMMARY

According to a first aspect, it is therefore provided a computer-implemented method of water management for an industrial site. The method comprises collecting data related to one or more exploitation scenarios of the industrial site. The collecting is performed via user-interaction. The method further comprises, for each respective exploitation scenario, computing, automatically by a computer system and based on the collected data, for each indicator of a plurality of indicators, a respective indicator value. The plurality of indicators comprises a first group of one or more water risk assessment indicators and a second group of one or more environmental footprint indicators. The first group of one or more water risk assessment indicators includes a physical water stress indicator and/or a physical water quality indicator. The second group of one or more environmental footprint indicators includes a carbon footprint indicator, a freshwater withdrawal indicator, a water scarcity footprint indicator, a COD indicator, a freshwater ecotoxicity indicator, a water withdrawal indicator, and/or a freshwater consumption indicator. The method further comprises displaying, simultaneously on a display of the computer system, a plurality of graphical representations. The plurality of graphical representations includes, for the indicator value of each indicator of the first group, a respective graphical representation. The plurality of graphical representations further includes, for the indicator value of each indicator of the second group, a respective graphical representation.

The method improves water management for an industrial site. Notably, the method provides a multi-criteria approach by displaying graphical representations of multiple indicator values. In addition, the indicators having a value of which a graphical representation is displayed comprise at least one water risk assessment indicator and at least one environmental footprint indicator. This specific combination of indicator categories being particularly relevant for water management for an industrial site, the method forms an improved assistance tool in this field. Furthermore, the fact that the indicator values are computed automatically and that the values of said specific combination are displayed simultaneously offers high ergonomics to the user.

The method according to the first aspect may comprise one or more of the following:
- the first group includes a physical water stress indicator and a physical water quality indicator, and the second group includes a carbon footprint indicator, a freshwater withdrawal indicator, a water scarcity footprint indicator, a COD indicator and a freshwater ecotoxicity indicator;
- the second group further includes a water withdrawal indicator and/or a freshwater consumption indicator;
- after the displaying, exploiting the industrial site based on the displaying and as a function of at least one of the one or more exploitation scenarios;
- the one or more exploitation scenarios comprise a first exploitation scenario and a second exploitation scenario, the plurality of graphical representations respective to the first scenario and the plurality of graphical representations respective to the second scenario being displayed simultaneously;
- the one or more exploitation scenarios comprise a first exploitation scenario and a second exploitation scenario, and, for the indicator value of one or more indicators of the first group and/or one or more indicators of the second group, the respective graphical representation respective to the first scenario and the respective graphical representation respective to the second scenario are displayed in a same respective chart;
- the respective graphical representations respective to the first scenario and the respective graphical representations respective to the second scenario are displayed superposed;
- the respective graphical representations respective to the first scenario and the respective graphical representations respective to the second scenario are displayed superposed on a radar chart;
- the radar chart comprises a first polyline in a first color representing indicator values of the first scenario and a second polyline in a second color representing indicator values of the second scenario, the first color and the second color being different;
- the radar chart is partitioned into a plurality of domains, wherein each domain delimits a respective range of values for each indicator represented in the radar chart;
- the displaying comprises a display of the radar chart adjacent to at least one histogram chart, wherein each histogram chart represents at least one parameter associated with a respective indicator represented in the radar chart;
- the first exploitation scenario and/or the second exploitation scenario include a water recycling process;
- the collected data related to at least one exploitation scenario comprise data representing a set of on-site processes, the computing including, for at least one indicator value, calculating a respective direct impact of the set of on-site processes and a respective indirect impact of the set of on-site processes;
- the data representing the set of on-site processes comprise on-site energy consumption data, on-site water flowrate balance data, on-site waste data, on-site chemical consumption, and/or composition of waste water;

the on-site waste data include effluent data;
the industrial site is an oil and/or gas industrial site, and the effluent data comprise one or more polycyclic aromatic hydrocarbons, one or more BTEX, one or more phenols, and/or one or more metals;
the plurality of graphical representations includes, for the at least one indicator value, a respective graphical representation which differentiates the respective direct impact and the respective indirect impact;
the collected data further comprise geographical data, the calculating of the respective indirect impact being based on the geographical data;
the computing includes accessing a conversion database, the calculating of the indirect impact being based on the conversion database; and/or
evaluating carbon neutrality of the industrial site and/or environmental neutrality of the industrial site.

It is further provided a computer program comprising instructions for performing the method.

It is further provided a computer readable storage medium having recorded thereon the computer program.

It is further provided a system comprising a processor coupled to a memory, the memory having recorded thereon the computer program.

According to a second aspect, it is provided a computer-implemented method of industrial management (for example process management for an industrial site, infrastructure management for an industrial site, product management for an industrial site and/or energy management for an industrial site). The computer-implemented method comprises collecting, via user-interaction, data related to one or more industrial scenarios. The method also comprises, for each respective industrial scenario, computing, automatically by a computer system and based on the collected data, for each indicator of a plurality of indicators, a respective indicator value. The method also comprises displaying, simultaneously on a display of the computer system, a plurality of graphical representations including, for each indicator value of one or more groups of the plurality of indicators, a respective graphical representation. Optionally, the method may comprise performing the industrial management based on the displaying and as a function of one or more industrial scenarios. While the method according to the first aspect focuses on water management, the method according to the second aspect broadens the scope of the presented technique to other technical fields, such as energy management and/or the management of a product manufacturing site. The product may be, for example, solar cells, a product derived from the oil and/or gas industry, a sub-product by manufacturing or any other applications that could apply to a circular economy approach. In examples, the plurality of indicators, the collecting, and/or the displaying is the same as in the method according to the first aspect or any example thereof. Also, a computer program, medium and system are provided as in the first aspect.

BRIEF DESCRIPTION OF THE DRAWINGS

Embodiments of the invention will now be described, by way of non-limiting example, and in reference to the accompanying drawings, where:
FIGS. 3-6 show screenshots of an example of the method according to the first aspect.

DETAILED DESCRIPTION

The method is computer-implemented. This means that steps (or substantially all the steps) of the method are executed by at least one computer, or any system alike. Thus, steps of the method are performed by the computer, possibly fully automatically, or, semi-automatically. In examples, the triggering of at least some of the steps of the method may be performed through user-computer interaction. The level of user-computer interaction required may depend on the level of automatism foreseen and put in balance with the need to implement user's wishes. In examples, this level may be user-defined and/or pre-defined.

A typical example of computer-implementation of a method is to perform the method with a system adapted for this purpose. The system may comprise a processor coupled to a memory and a graphical user interface (GUI), the memory having recorded thereon a computer program comprising instructions for performing the method. The memory may also store a database. The memory is any hardware adapted for such storage, possibly comprising several physical distinct parts (e.g. one for the program, and possibly one for the database).

Figure 1:
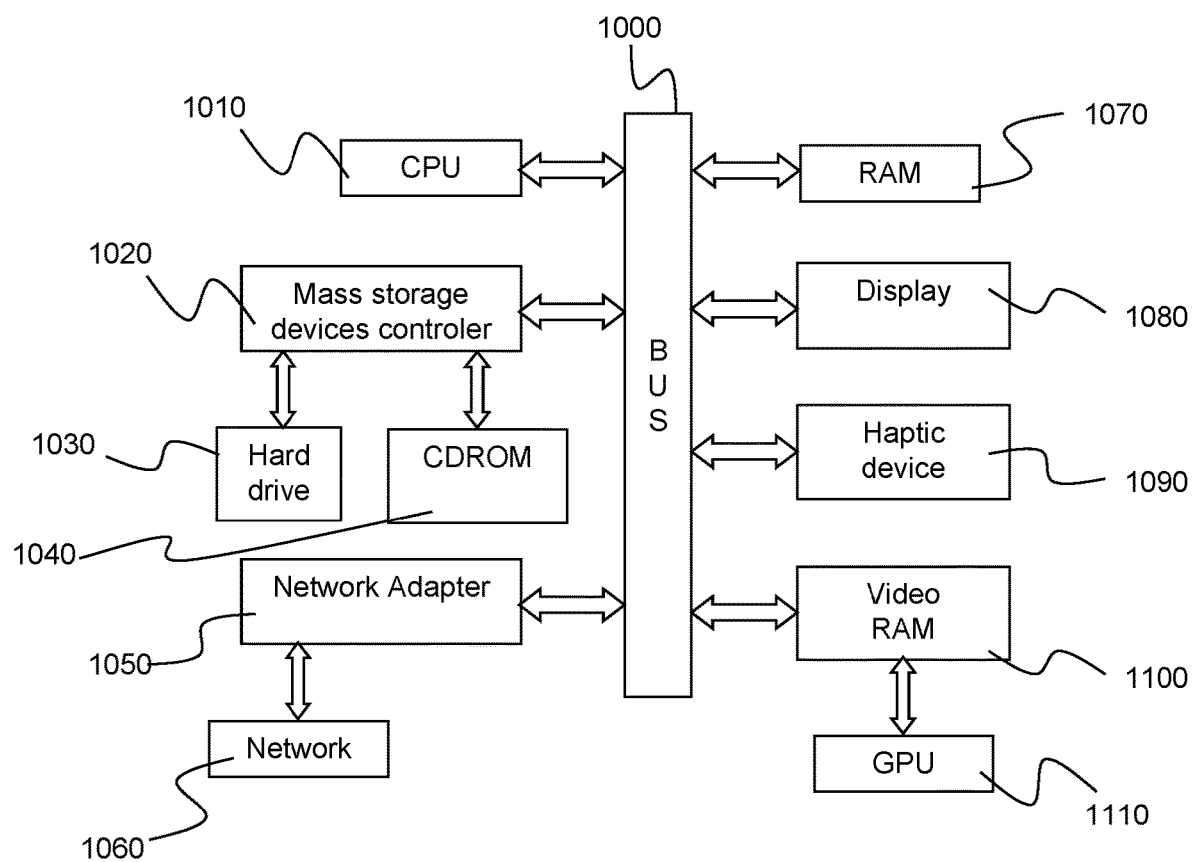
FIG. 1 shows an example of the system.

Referring to FIG. 1, the computer system of the example comprises a central processing unit (CPU) 1010 connected to an internal communication BUS 1000, a random-access memory (RAM) 1070 also connected to the BUS. In examples, the computer is further provided with a graphical processing unit (GPU) 1110 which is associated with a video random access memory 1100 connected to the BUS. Video RAM 1100 is also known in the art as frame buffer. A mass storage device controller 1020 manages accesses to a mass memory device, such as hard drive 1030. Mass memory devices suitable for tangibly embodying computer program instructions and data include all forms of nonvolatile memory, including by way of example semiconductor memory devices, such as EPROM, EEPROM, and flash memory devices; magnetic disks such as internal hard disks and removable disks; magneto-optical disks; and CD-ROM disks 1040; or any storage systems/means. Any of the foregoing may be supplemented by, or incorporated in, specially designed ASICs (application-specific integrated circuits). A network adapter 1050 manages accesses to a network 1060. The computer system may also include a haptic device 1090 such as cursor control device, a keyboard or the like. A cursor control device is used in the client computer to permit the user to selectively position a cursor at any desired location on display 1080. In addition, the cursor control device allows the user to select various commands, and input control signals. The cursor control device includes a number of signal generation devices for input control signals to system. Typically, a cursor control device may be a mouse, the button of the mouse being used to generate the signals. Alternatively or additionally, the client computer system may comprise a sensitive pad, and/or a sensitive screen.

The computer program may comprise instructions executable by a computer, the instructions comprising means for causing the above system to perform the method. The program may be recordable on any data storage medium, including the memory of the system. The program may for example be implemented in digital electronic circuitry, or in computer hardware, firmware, software, or in combinations of them. The program may be implemented as an apparatus, for example a product tangibly embodied in a machine-readable storage device for execution by a programmable processor. Method steps may be performed by a programmable processor executing a program of instructions to perform functions of the method by operating on input data and generating output. The processor may thus be programmable and coupled to receive data and instructions from, and to transmit data and instructions to, a data storage system, at least one input device, and at least one output device. The application program may be implemented in a high-level procedural or object-oriented programming language, or in assembly or machine language if desired. In any case, the language may be a compiled or interpreted language. The program may be a full installation program or an update program. Application of the program on the system results in any case in instructions for performing the method.

Figure 2:
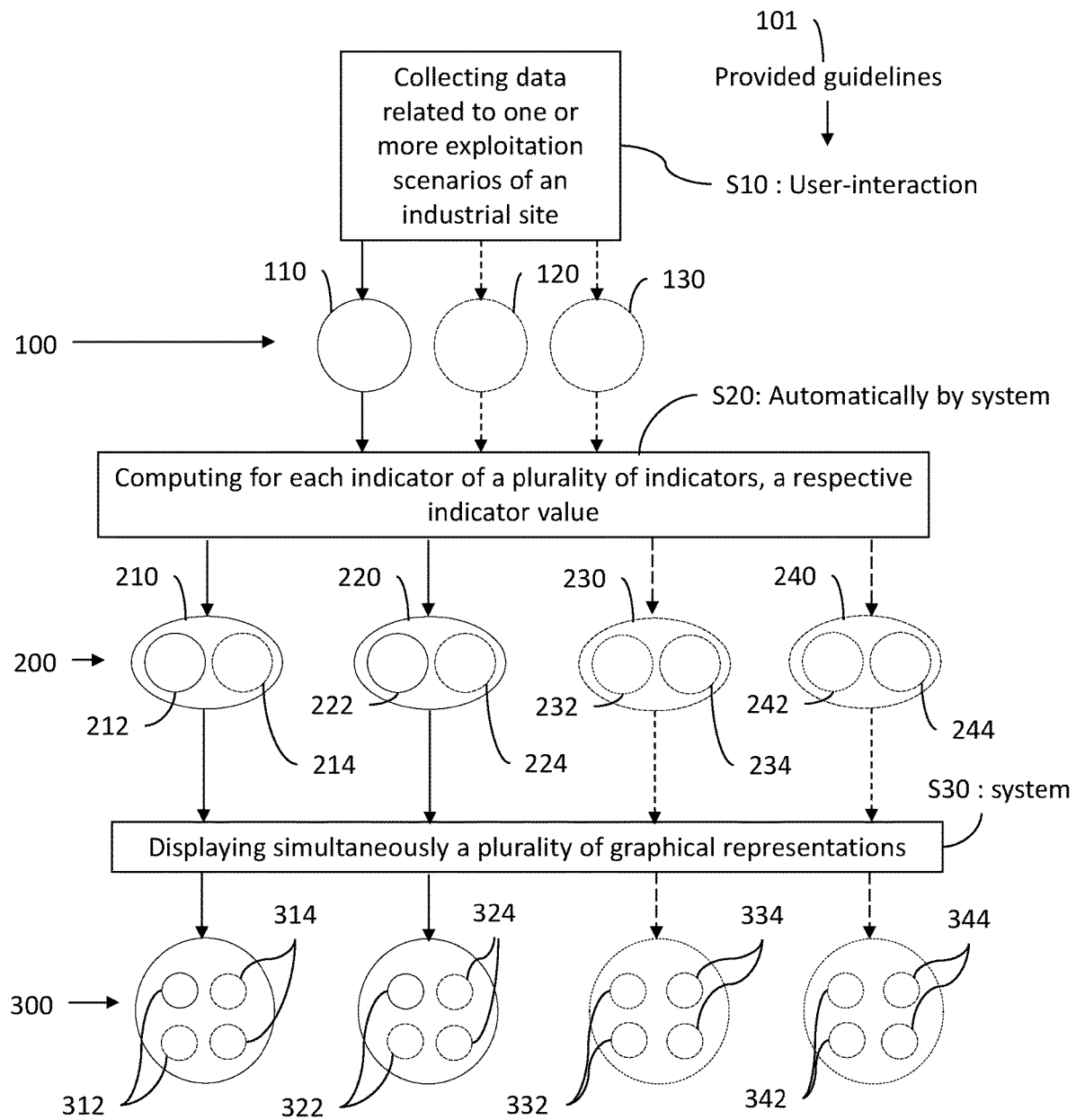
FIG. 2 shows a flowchart of an example of the method according to the first aspect.

Referring to FIG. 2, examples of the method according to the first aspect are now discussed.

The method involves user-interaction with a computer system. The method comprises collecting S10 via user-interaction data 100 related to one or more exploitation scenarios of the industrial site, including first data 110 related to a first exploitation scenario, and optionally second data 120 related to a second exploitation scenario (for example for comparison with the first exploitation scenario). Optionally, the collected data 100 may include one or more other data 130 each related to a respective other exploitation scenario. Guidelines 101 may be provided to the user to facilitate the user-interaction. The guidelines may include specific information for inputting information relative to an exploitation scenario.

The method comprises inputting the collected data 100 to a computing S20 which is then performed automatically by the system. In case there are several exploitation scenarios, the computing S20 is performed for each exploitation scenario. In such a case, the computing S20 may be executed independently on the collected data 110, 120 and/or 130 respective to each different exploitation scenario.

The computing S20 is now discussed with respect to one exploitation scenario. The method computes at S20, for each indicator of a plurality of indicators 200, a respective indicator value. In case the computing S20 is performed for several exploitation scenarios, the plurality of indicators 200 may be the same for all exploitation scenarios.

The plurality of indicators 200 comprises a first group 212 of one or more indicators of a water risk assessment indicator category 210 and a second group 222 of one or more indicators of an environmental footprint indicator category 220. Optionally, the plurality of indicators 200 may comprise another first group 214 of one or more indicators of a water risk assessment indicator category 210 and another second group 224 of one or more indicators of an environmental footprint indicator category 220. In other words, the computing S20 may optionally be performed for such optional indicators as well. Optionally, the plurality of indicators 200 may comprise one or more indicators of one or more other categories 230, 240, optionally including a third group 232 and/or another third group 234, and/or optionally including a fourth group 242 and/or another fourth group 244. In case the computing S20 is performed for several exploitation scenarios, such grouping of the plurality of indicators 200 may be the same for all exploitation scenarios.

The displaying S30 is now discussed with respect to one respective exploitation scenario. The method comprises, after the computing S20, displaying S30 simultaneously a plurality of graphical representations 300. The plurality of graphical representations 300 includes at least a respective graphical representation 312 for the indicator value of each indicator of the first group 212 and a respective graphical representation 322 for the indicator value of each indicator of the second group 222.

The user can thus visualize at least one indicator value of the water risk assessment indicator category 210 (corresponding to a respective graphical representation 312) and at least one indicator value of the environmental footprint indicator category 220 (corresponding to a respective graphical representation 322). This specific combination of indicators is particularly relevant for water management for an industrial site and assists the user in an ergonomic manner regarding their water management decision-making.

In examples, optionally the plurality of graphical representations 300 further includes at least a respective graphical representation 314 for the indicator value of each indicator of the other first group 214 and a respective graphical representation 324 for the indicator value of each indicator of the other second group 224. In this case, respective one or more indicator values are computed for the one or more indicators of the other first group 214 and respective one or more indicator values are computed for the one or more indicators of the other second group 224.

The user can thus visualize more indicator values of the water risk assessment indicator category 210 and of the environmental footprint indicator category 220. This gives additional information for performing water management of the site.

In examples, the at least a respective graphical representation 314 for the indicator value of each indicator of the other first group 214 and the at least a graphical representation 324 for the indicator value of each indicator of the other second group 224 may be displayed simultaneously along with the at least a respective graphical representation 312 for the indicator value of each indicator of the first group 212 and the at least a respective graphical representation 322 for the indicator value of each indicator of the second group 222. This allows to provide to the user indicator values of different groups in an ergonomic manner. Alternatively, the display of the at least a respective graphical representation 314 for the indicator value of each indicator of the other first group 214 and the at least a graphical representation 324 for the indicator value of each indicator of the other second group 224 may be toggled on and off. In examples, the user interacts with the system to toggle the display. This improves the ergonomics by not clogging the display.

In examples, the computing S20 is performed for optional indicators of one or more other categories 230, 240, including a third group 232 and optionally another third group 234, and including a fourth group 242 and optionally another fourth group 244. In this case, the plurality of graphical representations 300 includes at least a respective graphical representation 332 for the indicator value of each indicator of the third group 212 and a respective graphical representation 342 for the indicator value of each indicator of the fourth group 222, and optionally a respective graphical representation 334 for the indicator value of each indicator of the other third group 234 and a respective graphical representation 344 for the indicator value of each indicator of the other fourth group 244.

Such optional examples provide more indication to the user regarding the respective exploitation scenario and thus facilitates their water management decision-making.

In case the collecting S10 and the computing S20 are performed for several exploitation scenarios, the method may comprise, for each of said exploitation scenarios, displaying S30 a respective plurality of graphical representations 300. This allows comparison of different exploitation scenarios by the user. In particular, each respective plurality of graphical representations 300 may correspond to the same indicators. This allows comparison of different exploitation scenarios relative to a same list of indicators.

In examples, the plurality of graphical representations 300 respective to at least a first exploitation scenario and a second exploitation scenario may be displayed at S30 simultaneously. In other words, the plurality of graphical representations may be computed S20 and displayed S30 all at substantially the same time. This facilitates the comparison of different exploitation scenarios through their respective plurality of graphical representations (corresponding to respective computed indicator values). In examples, the plurality of graphical representations may all be displayed at S30 on a same screen. Alternatively, the user may scroll in a display in order for the plurality of graphical representations to be visible on said display (e.g. due to available space on the screen).

Alternatively or additionally, for each respective indicator of one or more (e.g. all) indicators involved at S30 (i.e. included among the indicators having a value whose graphical representation is displayed at S30), at least a first graphical representation respective to a first scenario and a second graphical representation respective to a second scenario may be displayed in a same chart at S30. In other words, a set of graphical representations including a graphical representation of at least one same indicator value for different exploitation scenarios may be displayed in a same chart at S30. Having a same reference on the same chart facilitates the comparison between the graphical representations. In addition, the displaying S30 may be simultaneous. This further facilitates the comparison of different exploitation scenarios. Alternatively, the displaying at S30 of the first and second graphical representations may be sequential.

In examples, the respective chart may include at least one axis. The respective graphical representation respective to the first scenario and the respective graphical representation respective to the second scenario displayed on the chart may share the at least one axis.

In examples the respective graphical representation respective to the first scenario and the respective graphical representation respective to the second scenario sharing an axis are displayed adjacent to one another. In examples, the respective graphical representations are spaced below a predetermined distance. In examples the predetermined distance may be less than 10% of the visible display. This is a particularly ergonomic display which allows the comparison of an indicator value among different exploitation scenarios. In such examples, the chart may optionally be a histogram.

In examples, the respective graphical representation respective to the first scenario and the respective graphical representation respective to the second scenario sharing an axis are displayed superposed (the respective graphical representation respective to the first scenario is displayed superposed over the respective graphical representation respective to the second scenario). This is a particularly ergonomic display allowing the comparison of indicator values corresponding to multiple indicators. In such examples, the chart may optionally be a radar chart.

Part of the graphical representations may be displayed superposed. For instance, part or all those sharing an axis may be displayed superposed. Alternatively, part or all graphical representations corresponding one to another in terms of indicators may be displayed superposed (i.e. two superposed graphical representations represent the same indicator).

In examples, the respective graphical representations respective to the first scenario and the respective graphical representations respective to the second scenario may be displayed superposed on a radar chart. The radar chart may display indicator values of the first scenario and the second scenario based on a plurality of radius axis, wherein each radius axis represents one indicator.

The radar chart improves the ergonomics of the display. Indeed, the user can directly compare indicator values of different scenarios in the radar chart. The radar chart is particularly adapted for such a multi-indicators comparison since several indicators and the values obtained for each indicator are represented in a single chart, which improves the analysis of the values for the user. Especially, the circular shape of the radar chart allows observing several indicators simultaneously since indicators are partitioned in the 360 degrees of the radar chart.

In examples, the radar chart may comprise a first polyline in a first color representing indicator values of the first scenario. The radar chart may comprise a second polyline in a second color representing indicator values of the second scenario. The first color and the second color may be different. A polyline may comprise a plurality of lines connecting the indicator values represented on each radius axis of the radar chart. The color of the second polyline or the first polyline may be blue, red, orange, green, yellow, black or grey. The first color and the second color may be contrasted.

The polyline improves the display of indicator values for the different scenarios. Indeed, such a representation allows quickly dissociating values of each scenario in the radar chart. Moreover, the use of different colors for each scenario allows a visual dissociation of the various scenarios.

In examples, the radar chart may be partitioned into a plurality of domains. Each domain may delimit a respective range of values for each indicator represented in the radar chart. For instance, the maximum range of values for each indicator may be subdivided into several portions. Then, domains may be formed based on the subdivided portion for each indicator. For instance, successive domains may be defined based on the successive portions defined for each indicator. Each domain may be associated to a level of acceptability. Thus, domains may represent a risk or a beneficial. Each domain may be represented with a respective color in the radar chart.

The partition into a plurality of domains improves the observation of the radar chart. Indeed, domains allow a direct observation of the compliance to given criteria. The radar chart with the plurality of domains gives a complete observation of different scenarios into a single display that includes, for each scenario, information about acceptability related to each indicator.

In examples, the displaying may comprise a display of the radar chart adjacent to at least one histogram chart. Each histogram chart may represent at least one parameter associated with a respective indicator represented in the radar chart. The histogram chart may comprise several bars associated to each scenario. A bar may represent value of the at least one parameter associated with an indicator. The histogram chart may comprise an axis with parameters values. The height of each bar may be associated to the axis and may represent the indicator value given by the axis. A bar may represent several parameters of the indicator. In this case, the bar height may represent a combination of values of the several parameters. For instance, in this case, the value of each parameter in the bar height may be separated from the others by a color code. The represented indicators in the at least one histogram chart may be a portion of indicators represented in the radar chart. For instance, two histogram charts may represent two indicators represented in the radar chart. The combination of the radar chart with the at least one histogram chart improves the ergonomics of the display. Indeed, the combination gives to the user a complete report of indicator values associated to each scenario in a single display. The radar chart allows a general understanding of indicator values for all scenarios. Each histogram chart gives a more precise display of indicator values for each scenario. Especially, each histogram chart may focus on given indicators of the radar chart, and the user may appreciate values of these given indicators more precisely in the at least one histogram chart.

In examples, multiple charts may be displayed at S30 (e.g. simultaneously) and may each comprise one or more graphical representations of the plurality of graphical representations 300.

In examples, a chart includes a graphical indication on a risk associated to water management corresponding to a displayed graphical representation of an indicator. In examples, the graphical indication may represent a configurable threshold for acceptability of the scenario regarding each of one or more indicator values, such as an indicator value for a physical water stress indicator. In examples, the graphical indication is determined based on user-defined data. In examples, the graphical indication may be color based. This facilitates the comparison between different graphical representations of different indicators among one and/or several exploitation scenarios.

In addition, the method may comprise comparing exploitation scenarios. Comparing exploitation scenarios may include defining a value of a global performance of each exploitation scenario. The global performance may be a function of the exploitation scenario and of the indicator values computed for the exploitation scenario. The comparison between exploitation scenarios may include a comparison based on the respective global performance for each compared exploitation scenario.

In examples, after the displaying S30, the method may include exploiting the industrial site (e.g. real-world industrial site) based on the displaying S30 and as a function of at least one of the one or more exploitation scenarios. In other words, the computer-implemented method may be included in a process of assessment of one or more exploitation scenario against the indicators involved at S30. The process may then include truly exploiting the industrial site based on this assessment. The exploitation is a function of at least one or more of the exploitation scenarios. In other words, the exploitation parameters truly applied in reality are a function of the parameters retained for at least part of the exploitation scenarios simulated by the computer-implemented method. For example, the parameters may be equal to the parameters of the exploitation scenario simulated as having the best global performance.

In such a case, the process may include performing the method of FIG. 1 for several exploitation scenarios, selecting (e.g. by a user) the exploitation scenario having the best global performance based on the displaying S30 (e.g. according to any global performance function), and then exploiting the industrial site according to the selected exploitation scenario.

An exploitation scenario of an industrial site is a set of one or more processes and/or one or more infrastructures for operating the site. In the case of the method, the one or more processes may comprise any one or any combination of a water withdrawal process, a water treatment process, wastewater treatment process, water recycling process, water reuse process, water treatment process for utilities, and water discharge process. The one or more infrastructures may comprise any one or any combination of a water withdrawal infrastructure, a water treatment infrastructure, a wastewater treatment infrastructure and a water discharge infrastructure. In examples, the industrial site is configured for producing a product manufactured by the site. In examples, the manufactured product may be electricity, a petroleum product, a product derived from gas, solar panels (or parts thereof such as solar cells), chemicals involved in the oil and gas industry, transformation industries and/or new energies and storage. In examples the site may be an oil and/or gas industrial site. In such examples, the method is particularly relevant since water is involved in the manufacture of any of the listed products and the method enables an improved water management of the site, increasing productivity of the site.

The first group 212 of one or more water risk assessment indicators may include a physical water stress indicator or a physical water quality indicator, or yet both such indicators. The physical water stress indicator measures the importance of water for the site and the probability for the site to be under water stress (such as lack of water). The physical water quality indicator measures the importance for the site to discharge its water, and the risk to impact the receiving body which may lead to being unable to discharge. Either of these two water risk assessment indicators accurately estimates a water risk associated to a process and/or infrastructure of the site.

The second group 222 of one or more environmental footprint indicators may include a carbon footprint indicator, a freshwater withdrawal indicator, a water scarcity footprint indicator, a chemical oxygen demand (COD) indicator, a freshwater ecotoxicity indicator, a water withdrawal indicator or a freshwater consumption indicator, or any combination (e.g. all) of such indicators. Any one of the previously listed environmental footprint indicators is particularly relevant for the exploitation processes.

Notably, the carbon footprint indicator measures direct and indirect emission of CO2 (e.g. from energy, chemicals, waste and/or infrastructure) of the exploitation scenario which is particularly relevant for the environmental footprint. The freshwater withdrawal indicator measures direct and indirect volume of freshwater withdrawn by the site, which is relevant to water management since volume changes on water sources (e.g. natural water sources) may negatively affect the environment. The water scarcity footprint indicator corresponds to direct and indirect volume of water consumed by the site multiplied by a water stress index, the water stress index may be determined from the water stress index of each geographical zone where the water was consumed. The COD indicator measures direct and indirect release of COD into receiving water body, which is particularly relevant for exploitation scenarios with water discharge processes. The freshwater ecotoxicity indicator measures direct and indirect impact of the substances discharged into the receiving water body, which is particularly relevant for the environmental footprint. The water withdrawal indicator measures direct and indirect volume of water withdrawn by the site. The freshwater consumption indicator measures direct and indirect volume of freshwater consumed by the site.

The displaying S30 simultaneously displays a respective graphical representation 312 for the indicator value of any one of the water risk assessment indicators of the first group 212 and a respective graphical representation 322 for the indicator value of any one of the environmental footprint indicators of the second group 322. This allows a synthetic and pertinent assessment of the exploitation scenario in an ergonomic manner.

In examples, the first group 212 includes both a physical water stress indicator and a physical water quality indicator, and the second group 222 includes all among a carbon footprint indicator, a freshwater withdrawal indicator, a water scarcity footprint indicator, a COD indicator and a freshwater ecotoxicity indicator. Thus, displaying S30 simultaneously the plurality of graphical representations 300 includes displaying simultaneously respective graphical representations of the indicator values for all of the indicators of the first group 212 and all of the indicators of the second group 222. This particular combination of indicator values provides a broad and complete representation of the exploitation scenario and improves water management of the site. In examples, the graphical representations of the indicator values for all of the indicators of the first group 212 and all of the indicators of the second group 222 are simultaneously displayed in a same chart, the chart including one or more graphical indications representing (e.g. respectively) one or more configurable thresholds.

In examples, the second group of environmental footprint indicators further includes a water withdrawal indicator and/or a freshwater consumption indicator.

This gives additional information providing to the user a representation of the exploitation scenario which is even more complete.

The global performance of an exploitation scenario determined from the indicator values for listed indicators of the water risk assessment category 210 and the listed indicators of the environmental footprint category 220 may enable identification and modification of the one or more processes and/or one or more infrastructures of the exploitation scenario.

Indeed, each process/infrastructure of the exploitation scenario may be associated to a respective predetermined set of one or more parameters and defined by a respective set of one or more values each of a respective parameter. Each exploitation scenario may thus comprise respectively such a parameter value set.

The user may modify a value of a parameter of the set of one or more parameters based on the global performance of the exploitation scenario. This allows to improve the water management of the site.

In examples, the exploitation scenario includes a parameter on the location of wastewater discharge, one or more parameters on COD removal and one or more parameters on water flux. Following the determination of the calculation and display of one or more ecological footprint indicators, the user determines the global performance of the exploitation scenario and identifies that the removal rate of COD in discharged water is insufficient. The different water flux of the exploitation scenario are characterized from a physico-chemical analysis and mass balance is determined (e.g. for Cupper, Silicon and/or other chemicals involved with effluents). A new exploitation scenario is determined with different parameters which comprises an increased removal rate of the COD, which improves water management of the exploitation scenario. Thus, the use and modification of parameters in the parameters aids in determining improved exploitation scenarios. This improves water management of a site. The user may then modify the physical industrial site accordingly. Thus, water management of the site is improved.

In examples, the water quality of discharged water is automatically calculated according to predetermined water treatment objectives.

Optionally, the user may repeat the method after modifying the exploitation scenario in order to determine a global performance of the new modified exploitation scenario. The user may iteratively modify one or more parameters (e.g. modifying a value of a parameter and/or adding new parameters describing other processes/infrastructures) of the exploitation scenario and perform the method at each iteration. The user may continue the iteration until the global performance of the exploitation scenario becomes optimal. The determination of an optimal exploitation scenario may be based on a set of values. The set of values may be defined by the user. Alternatively, the user may continue the iteration for a given fixed number of iterations which may be user-defined. Such iterations may enable the determination of an exploitation scenario with an improved water management.

In examples, an exploitation scenario may comprise modules. Each module may correspond to an activity of the industrial site involving water. The combination of the modules may thus reproduce, from beginning to end, the lifecycle of water inside the industrial site. Collecting S10 data 100 may be based on the modules. In other words, respective data from each module may be collected independently.

Additionally or alternatively, in case there are several exploitation scenarios, the process/infrastructure sets of the different exploitation scenarios may be two-by-two different (i.e. the respective parameter value sets for at least one process/infrastructure are different, and/or a process/infrastructure present for one exploitation scenario is absent for the other exploitation scenario). In examples, a comparison of the several exploitation scenarios may be performed according to the method. In such examples, the comparison may include comparing a respective global performance for each exploitation scenario. In examples, the several exploitation scenarios may include a first exploitation scenario and a second exploitation scenario. The first exploitation scenario and the second exploitation scenario may comprise respective one or more processes/infrastructures associated with respective computed indicator values. A comparison between the indicator values of the first exploitation scenario and the second exploitation scenario may result in identifying an improvement over one or more indicators of the first exploitation scenario in the second exploitation scenario. The improvements may result from an additional and/or alternative process/infrastructure of the second exploitation scenario relative to the first exploitation scenario. The comparison may further include implementing on the physical site the additional and or alternative process/infrastructure of the second exploitation scenario.

Notably, in examples, the first exploitation scenario and/or the second exploitation scenario may include a water recycling process. In examples where both the first exploitation scenario and the second exploitation scenario include a water recycling process, the water recycling process for each exploitation scenario may be different (e.g. different values are associated to the water recycling process, different parameters define the water recycling process, and/or different infrastructure is associated to the water recycling process). The exploitation scenario containing the water recycling process may be determined as having an improved water management, based on the computation of respective indicator values and display of respective graphical representations. The improvement on water management may be due to the water recycling process. Thus, the process is added to the exploitation scenario of the site and may be added to the physical site.

In examples, the first exploitation scenario corresponds to a current exploitation scenario being performed on a physical site (e.g. real-world site), the first exploitation scenario may be a baseline scenario from which other scenarios may be compared. The second exploitation scenario corresponds to an alternative exploitation scenario which may be applied to the physical site. This improves water management of the site by computing values for indicators taking into account the changes to the processes/infrastructures on the physical site.

Notably, in examples, one or more indicator values of an alternative scenario may be computed using a first scenario as a baseline. In such a case, an indicator value corresponding to the first exploitation scenario may be subtracted from the indicator value corresponding to a same indicator of a second exploitation scenario. This facilitates the comparison between exploitation scenarios.

In addition, the collected data 100 related to at least one exploitation scenario, (e.g. the first exploitation scenario and/or the second exploitation scenario, possibly all exploitation scenarios) may comprises data representing a set of on-site processes. On-site processes may be processes which are performed directly on the site according to the exploitation scenario. In such a case, the computing S20 includes calculating, for at least one indicator value, a respective direct impact of the set of on-site processes and a respective indirect impact of the set of on-site processes. A direct impact may be a contribution to the computation of a value of an indicator which stems from a process and/or a product performed/produced inside the site. For example, a volume of water withdrawn (e.g. when performing a process in the site) has a direct impact on a water withdrawal indicator since the volume of water withdrawn by the site is a process performed in the site. An indirect impact may be a contribution to the computation of a value of an indicator which stems from a process and/or a product performed/produced outside the site (off-site) but which is required in the exploitation scenario of the site. For example, energy (e.g. electricity) is consumed for a process of the exploitation scenario of the site to be performed, however the energy consumed may not be produced by the site but is rather received through cables and/or other sources external to the site. The production source of the consumed energy may be fossil fuels. Therefore, energy consumption by the process of the exploitation scenario has an indirect impact on a carbon footprint indicator of the exploitation process due to the origin of the consumed energy. The computation S20 thus takes into account broad parameters and inter-relations between the collected data 100. This improves water management as the computed values for the plurality of indicators are more accurate.

Additionally or alternatively, the collected data 100 may further comprise geographical data. In such a case, the calculation of a respective indirect impact during the determining S20, may be based on the geographical data. Geographical data may include information identifying a specific geographical location and/or information determining a distance. For example, the collected data may include information on a chemical not produced by the site and consumed in the exploitation scenario. The information may comprise production location of the chemical and transportation means used to route the chemical to the site. During the determining of an indicator value for a carbon footprint indicator, the CO2 emitted during the transportation of the chemical may be taken into account.

Notably, the computing S20 may include accessing a conversion database for calculating an indirect impact when computing a respective indicator value for a plurality of indicators. The calculating of the indirect impact may be based on the conversion database.

Notably, an indicator value of an indicator may correspond in part to data of an on-site process directly affecting the indicator and data related to another on site process indirectly affecting the indicator. In such a situation, the computation of the indicator value includes converting the data of the other on-site process to equivalent data with respect to the data of the on-site process affecting the indicator. In examples, the conversion may be performed through a conversion table. In examples, the indicator value is computed from an algebraic sum of the converted data and the data of the on-site process directly affecting the indicator. This allows taking into account a greater number of sources when computing an indicator value which results in a more accurate indicator value. This improves water management of a site.

Notably, the data 100 collected at S10 may include only on-site data and/or geographical data. Thus, off-site data is not necessarily collected but is still taken into account by accessing the database. This facilitates water management of the site.

In examples, the conversion database may be ecoinvent 3.3.

The data representing the set of on-site processes may comprise on-site energy consumption data, on-site water flowrate balance data, on-site waste data, on-site chemical consumption, and/or composition of waste water. These data are particularly relevant for the computation of indicator values associated to water management. Notably, the listed data is particularly relevant to the computation of indicator values for indicators including physical water stress indicator, a physical water quality indicator, a carbon footprint indicator, a freshwater withdrawal indicator, a water scarcity footprint indicator, a COD indicator, a freshwater ecotoxicity indicator, a water withdrawal indicator and/or a freshwater consumption indicator.

The waste data may include effluent data. In examples, effluent data may comprise one or more polycyclic aromatic hydrocarbons, one or more BTEX (in other words, one or more benzene compounds, one or more Toluene compounds, one or more Ethylbenzene compounds and/or one or more Xylene compounds), one or more phenols (e.g. one or more phenol compounds), and/or one or more metals (e.g. copper, lead, magnesium and/or iron). Such effluent data is common in oil and/or gas industrial sites. The collecting of such effluent data when the exploitation scenario is for an oil and/or gas industrial site allows precise computation of indicator values. Therefore, water management of the site is improved.

In addition, during the displaying S30, the plurality of graphical representations 300 may include, for the at least one indicator value, a respective graphical representation which differentiates the respective direct impact and the respective indirect impact. The differentiation may correspond to the proportion of the indicator value which results from the respective indirect impact and the proportion of the indicator value which corresponds to the direct impact. This particular display allows the user to understand the contributions of the collected data 100 to a computed indicator value. In examples, a tag identifying the data from which the indirect impact and/or the direct impact is calculated is also displayed.

Notably, the indirect impact associated to a process/infrastructure of an exploitation scenario may intervene counterintuitively during the calculation of an indicator value. In examples, a specific water treatment process, requiring chemicals, may improve a COD indicator but also increase the indicator value of a carbon footprint indicator. The production of the chemicals and their transportation to the site may produce CO2 which ultimately may make the global performance of the exploitation scenario worse than another exploitation scenario where the specific water treatment process is not performed. The differentiation of a respective indirect impact and a respective direct impact on a graphical representation displayed thus enables the user to understand how the different processes affect, directly or indirectly the indicators. This improves water management of the industrial site.

In examples, indicator category 230 comprises economic performance indicators, and/or indicator category 240 comprises social impact indicators.

In examples, the water risk assessment indicators 210 (e.g. in particular group 212) include any combination (e.g. all) of the following indicators:
Physical water stress;
Physical water quality;
Regulatory;
Reputational; and/or
Technological risk.

In examples, the environmental footprint indicators 210 (e.g. in particular group 222) include any combination (e.g. all) of the following indicators:
Carbon footprint;
Freshwater withdrawal;
Water scarcity footprint;
COD;
Freshwater ecotoxicity and/or
Ecotoxicity for discharge in other environments (such as sea water, aquifer, and/or water with a salinity rate higher that 2 g/L).

In examples, the economic performance indicators 230 (e.g. in particular group 232) include any combination (e.g. all) of the following indicators:
CAPEX;
OPEX;
PBP; and/or
LCOW.

In examples, the social impact indicators 240 (e.g. in particular group 242) include any combination (e.g. all) of the following indicators:
Employment;
Local acceptance; and/or
Burdens on local population.

In examples and as discussed earlier, the method may comprises displaying at S30 values for all these indicators and for one or more exploitation scenarios. And the collected data 110-130 may comprise all data necessary to compute these indicators. This provides a global view on performance of the exploitation scenarios.

In examples, the method may further comprise evaluating carbon neutrality of the industrial site and/or environmental neutrality of the industrial site. Evaluating carbon neutrality of the industrial site and/or environmental neutrality may comprise:
Evaluating whether or not neutrality is met; and/or
Assessing a neutrality performance (i.e. measuring how neutral the site is).

The carbon neutrality refers to achieving net zero carbon dioxide emissions by balancing carbon emissions with carbon removal (often through carbon offsetting) or simply eliminating carbon emissions altogether. Environmental neutrality refers to the achievement of a zero environmental impact. Environmental neutrality can be more generic than carbon neutrality. In this case, the evaluating of environmental neutrality can refer to the neutrality evaluation of any kind of emissions, such as carbon emissions but also possibly other emissions than carbon emissions. Alternatively, environmental neutrality can also be more global than carbon neutrality. In this case, the evaluating of environmental neutrality may refer to the overall emissions neutrality evaluation of the industrial site. The evaluating of environmental neutrality may comprise the neutrality evaluation of several (e.g. all) emissions of the industrial site.

The method may comprise evaluating carbon/environmental neutrality according to the one or more exploitation scenarios of the industrial site. For instance, the method may comprise evaluating carbon/environmental neutrality of one current exploitation scenario. The method thereby allows evaluating the current neutrality of the industrial site. Alternatively, the method may comprise evaluating carbon/environmental neutrality of the industrial site according to several exploitation scenarios. In this case, the method allows comparing the several exploitation scenarios with respect to said neutrality.

Evaluating environmental/carbon neutrality may be based on the display. For instance, environmental/carbon neutrality may be based on the simultaneous (or superposed) display of the plurality of graphical representations.

After the evaluating of environmental/carbon neutrality, the method may further comprise modifying the exploitation to improve or reach neutrality of the industrial site. Alternatively, the method may further comprise, after the evaluating of environmental/carbon neutrality, retaining the better exploitation scenario with respect to neutrality for the industrial site.

The method should help to the monitoring of the carbon/environmental emission and to the carbon/environmental neutrality.

FIG. 3-6 illustrate an example of the method.

FIG. 3 shows an example of a GUI 30 for collecting S10 data 110' related to a first exploitation scenario. The GUI comprises input fields 31' for example for data associated to a sludge management (liquid waste management) process of an industrial site. At S10, the data is collected through user input and the input fields are filled. The GUI further comprises pieces of information 32'. A value of a piece of information forms data and is collected with a respective input field 31'. The pieces of information may include a geographical piece of information 33' (here "transportation distance"). A value of the geographical piece of information 33' forms geographical data.

FIG. 4 shows an example of a plurality of indicators 200' whose respective indicator values are calculated at S20 (here the values are all set to zero, only for the purpose of illustration). Notably, FIG. 4 shows two categories of indicators including a water risk assessment category 210' and an environmental footprint category 220'. A first group 212' of water risk assessment indicators which includes a physical water stress indicator and a physical water quality indicator is further shown. In addition, another first group of water risk assessment indicators 214' is also shown, this other group includes a regulatory indicator, a reputational indicator and a technological risk indicator (e.g. technological readiness level indicator which measures the risk associated to the maturity of the technology of the site). A second group 222' of environmental footprint indicators is also shown. Values for the plurality of indicators are calculated in this example for a baseline exploitation scenario and three alternative scenarios. The indicators may be calculated for different exploitation scenarios. FIG. 4 shows four different exploitation scenarios, a baseline exploitation scenario and three other exploitation scenarios. Any of the exploitation scenario may include a water recycling process.

Figure 5:
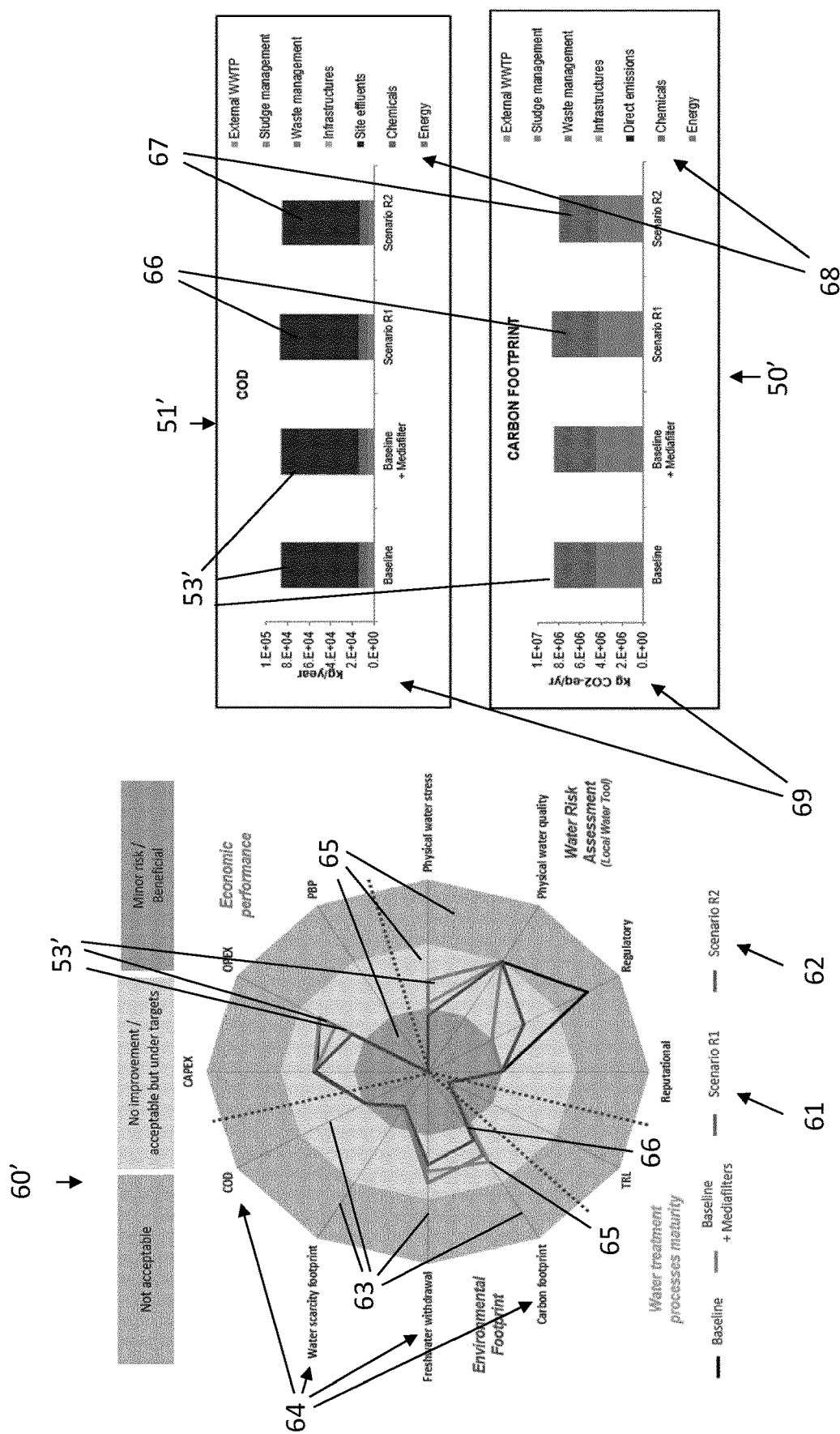

FIG. 5 shows an example of different charts used to simultaneously display at S30 a plurality of graphical representations 53'. Charts 50' and 51' are histograms. Chart 51' histogram corresponds to a chart on which the respective graphical representations for the indicator value of a COD indicator in a first baseline exploitation scenario and three other exploitation scenarios may be displayed, for example simultaneously. In such a case, the graphical representations 53' are displayed adjacent one to the other. Histogram 50' corresponds to a carbon footprint histogram. Both histograms may be displayed simultaneously in a same computer screen. The histograms may include one or more threshold values per parameter for definition of acceptability according to internal criteria or external criteria (e.g. regulations and specifications/discharge limits). Chart 60' is a radar chart on which it is simultaneously displayed graphical representations 53' of indicator values each respectively corresponding to an indicator belonging to one of four different categories. In chart 60', each category includes multiple indicators and for each indicator a graphical representation is displayed simultaneously. In addition, graphical representations for all indicator values in chart 60' are displayed simultaneously for four different exploitation scenarios. The four exploitation scenarios correspond to a baseline exploitation scenario and three other exploitation scenarios. In examples, the graphical representations associated to a particular exploitation scenario may be displayed on its own or with graphical representations of other specific exploitation scenarios (for example according to user selection). In chart 60' a color code indicates to the user the degree of risk associated with an indicator value.

The respective graphical representations respective to the first scenario (scenario R1) 61 and the respective graphical representations respective to the second scenario (scenario R2) 62 are displayed superposed on a radar chart 60'. The radar chart 60' displays indicator values of the first scenario 61 and the second scenario 62 based on a plurality of radius axis 63, wherein each radius axis 63 represents one indicator 64. The radar chart 60' comprises a first polyline 65 in a first green color representing indicator values of the first scenario 61. The radar chart 60' comprises a second polyline 66 in a second blue color representing indicator values of the second scenario 62. The first green color and the second blue color are different. The first polyline and the second polyline comprise a plurality of lines connecting the indicator values represented on each radius axis of the radar chart. The first green color and the second blue color are contrasted. The radar chart 60' is partitioned into three domains 65 (represented in red, yellow and green). Each domain 65 delimits a respective range of values for each indicator 64 represented in the radar chart 60'. The maximum range of values for each indicator 64 is subdivided into three portions. In this example, domains represent an acceptability level of indicators. The red domain represents a "not acceptable" area. The yellow domain represents a "no improvement/acceptable but under targets" area. The green domain represents a "minor risk/beneficial" area. The displaying comprises a display of the radar chart 60' adjacent to two histogram charts 50', 51'. The first histograms chart 50' represents the "CARBON FOOTPRINT" indicator for the first scenario 61 and the second scenario 62. The second histogram chart 51' represents the "COD" indicator for the first scenario 61 and the second scenario 62. The "CARBON FOOTPRINT" indicator and the "COD" indicator are also represented in the radar chart 60'. Each histogram chart comprises a first bar 66 associated to the first scenario 61 and a second bar 67 associated to the second scenario 62. Each bar represents seven parameters 68 associated with indicators. Each histogram chart comprises an axis 69 with parameters values. The height of each bar 66, 67 is associated to the axis 69 and represents the indicator value given by the axis 69. The bar height represents a combination of values of the seven parameters 68. The value of each parameter 68 in the bar height is separated from the others by a color code for each parameter (via the scale of each histogram chart 68). The radar chart 60' and the two histogram charts 50', 51' improve the ergonomics of the display.

Figure 6:
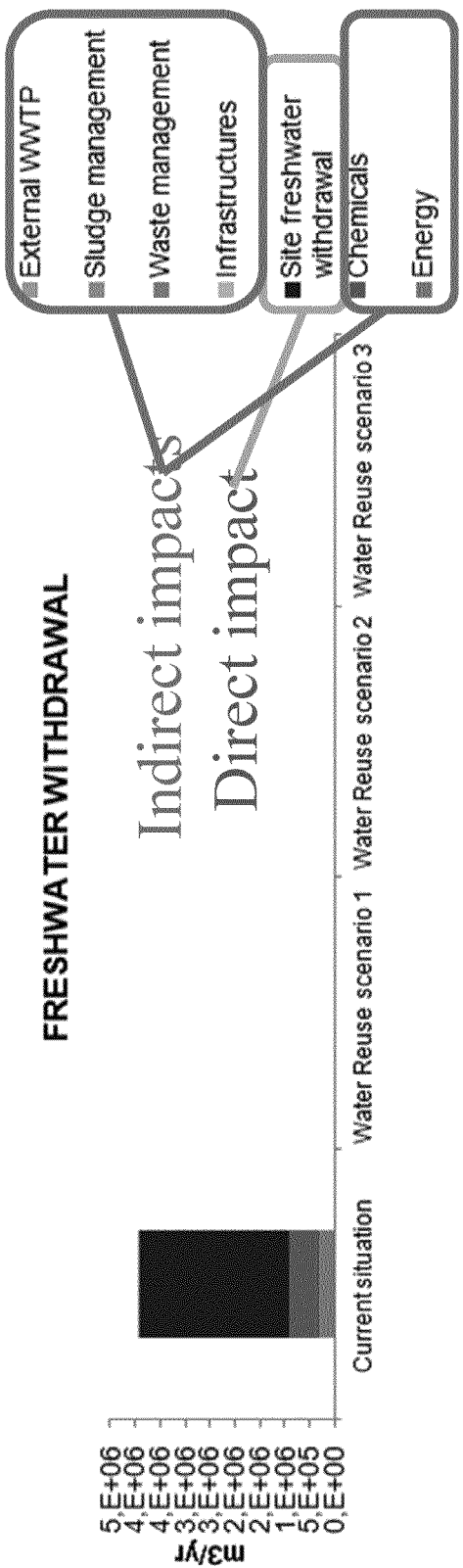

FIG. 6 shows an example of a graphical representation displayed at S30 for the indicator value of a freshwater withdrawal indicator. The graphical representation differentiates the contribution of direct and indirect impacts to the indicator value. Notably, in the example of FIG. 6, the direct impact is calculated from site freshwater withdrawal data which is on-site data. The indirect impact is calculated by accessing a conversion database and from chemicals data and energy data. In examples, the indirect data may also be calculated from geographical data. Each contribution may be proportionally displayed. In addition, the contribution to the indicator value for each data may be displayed. This example is discussed with reference to FIG. 6 and a freshwater withdrawal indicator, but it may apply to calculated indicator values for any indicator.

Other examples of the method are now discussed.

In examples, the method is applied to a site and the current water management of the site serves as a basis for one or more alternative water management scenarios that are studied according to the invention. For example, water on the site may be managed to ensure a year of production, respecting local regulation.

The method automatically calculates indicators associated with water risk assessment and environmental footprint of an exploitation scenario of a site. In addition, other categories of indicators may also be automatically calculated, such as social impact indicators and/or economic performance indicators for the site.

In the following, examples of indicators associated with certain categories of indicators are discussed.

Economic performance indicators.

The calculated economic performance indicators may include any one or more of:
- capital expenditures (CAPEX), which is an indicator that covers all investments required for water use;
- Operational Expenses (OPEX), which is an indicator that covers all expenses related to water management (e.g. expenses related to wages, energy, reactants, water purchase and/or water disposal);
- net present value (NPV), this indicator is calculated relative to a baseline, the baseline may be defined by one of the exploitation scenarios considered, for example the current management of the site;

internal rate of return (IRR), this indicator is the discount rate that makes the net present value (NPV) equal to zero and characterizes the economic viability of the project;

Leveled water cost (LCoW), this indicator corresponds to the cost of the managed water (for example in euros/m3) and is typically calculated after the water treatment involved in the site process; and payback period, this indicator is associated with the period required to recoup the funds expended in the investment (for example in years) and is calculated in comparison to the current situation.

Indicators Associated with the Environmental Footprint.

The calculation of environmental footprint indicators is based on the Life Cycle Assessment (LCA) methodology. In examples, the indicators can be based on ISO 14'040-44-46 standard on LCA and water footprint.

Indicators enable metric-based assessment and generate quantified results. In addition, the indicators take into account the impact of multiple sources. It possible to take into account all product stages "from cradle to grave", due to the life-cycle orientation.

In examples, environmental footprint indicators can be separated into groups. In examples, the groups correspond to climate change, water pollution and water consumption. In examples, the climate change group includes indicators associated with global warming. In examples, the water pollution group includes indicators associated with the chemical oxygen demand (COD) and/or the ecotoxicity of freshwater. In examples, the water consumption group includes indicators associated with water withdrawal, freshwater withdrawal, freshwater consumption and/or water scarcity footprint.

Among the indicators of the environmental footprint, there may be one carbon footprint indicator. This indicator quantifies direct and indirect CO2 emissions (energy, chemicals, waste, infrastructure, etc.) due to the water management scenario.

In the following example, one or more carbon footprint indicators are calculated from site energy data (e.g. energy consumption and/or generation), production/transport of chemicals, and site infrastructure and/or sludge/waste management of the site. This allows to separate the calculation of indicators for energy carbon footprint, carbon footprint of chemicals, carbon footprint of infrastructure and carbon footprint of sludge management, respectively. In addition or alternatively, one or more indicators taking into account all previous carbon footprints may be calculated.

For example, when calculating the energy carbon footprint, the user first collects data on: the consumption/production of electricity on the site, consumption/production of natural gas on the site and/or consumption/production of fuel on the site. In addition, biogas valorization data on-site and/or off-site may also be collected. An indicator corresponding to the carbon footprint of energy is then automatically calculated based on the collected data.

In another example, when calculating the carbon footprint of chemicals, the user first collects data on the chemicals used in the site. These data may include the type of reactant, mass content, source and/or transport distance (road, sea, river, train, airplane). Notably, the transport distance is a geographical datum allowing calculations of the indirect impact in a given scenario (such as the indirect impact of chemicals). For example, the transport of chemicals produces a carbon footprint that is considered a contribution of the chemical and is often overlooked because it is not directly produced by the chemical itself. After collecting the data, an indicator corresponding to the carbon footprint of chemicals is calculated.

The system is configured to interact with a database to calculate the emission factor corresponding to the data entered by the user. In examples, the emission factor is used to calculate an indicator of a corresponding carbon footprint. Calculations are done after or during the collection of data. In examples, the database may be ecoinvent 3.3. The database allows calculation of the electricity emission factor using country mix average data. In addition or alternatively, the system can compare the calculated indicators with the regional emission factors, for example by using global emission factors or European averages.

In another example, infrastructure carbon footprint is calculated. The calculation requires collecting data on the quantity of material required for the infrastructure. The materials may include steel, iron, aluminum, concrete and/or plastic. When calculating the infrastructure carbon footprint, the amortization period is considered. In other words, the project time horizon is taken into account.

In another example, carbon footprint of sludge management is calculated. The calculation requires collecting data on one or both sludge management routes among incineration and landfill. Data is collected for each considered route on: quantity of wet matter, dry matter content, fossil carbon content and/or the transportation distance. In addition, if the incineration route is taken into account, the user also enters data relating to a lower heating value. In addition or alternatively, if the landfill route is considered, degradable carbon data is also entered by the user.

In addition, among the calculated environmental footprint indicators, there may be at least one freshwater withdrawal indicator and/or one water scarcity footprint indicator. The freshwater withdrawal indicator quantifies the direct and indirect freshwater volumes collected by the site, while the water scarcity indicator is the direct and indirect volume of water consumed by the site multiplied by the water stress index of each geographical area where the water was consumed. These last two indicators may belong to the group of water consumption indicators.

In examples, the computation of indicator values for freshwater withdrawal and water scarcity take into account indirect use of water. Indeed, energy production, chemical production, infrastructure production and/or transportation require a certain amount of water. In order to take into account the indirect use of water, the input data corresponding to said productions and transportation are converted using a database accessed during the computation of indicator values. In examples, the database can be ecoinvent 3.3.

In examples, the water scarcity index used for calculating the water scarcity footprint indicator is regionalized.

In examples, the indirect use of water may include chemicals or other resources from areas other than the area of the site. By default, the water stress index used may be the water stress index of the site. This default value may correspond to the country average. However, when calculating the water scarcity footprint indicator, several values for different water stress indices may be required. For example, if the indirect use of water from chemicals is calculated, the user can apply an average water stress index of the country of origin to account for different geographical locations. In addition, if geographic information is known, a site-specific value for the water stress index can be used instead. This makes it possible to more accurately calculate the scarcity footprint indicator of the water resource taking into account geographic data.

In examples, a water withdrawal indicator and a freshwater consumption indicator can also be calculated. The water withdrawal indicator quantifies the direct and indirect volume of water withdrawn from the site, while the freshwater consumption indicator quantifies the direct and indirect freshwater volume consumed by the site.

In addition to a carbon footprint indicator, a freshwater withdrawal indicator and a water scarcity indicator a COD indicator and/or a freshwater ecotoxicity indicator may be computed. These two indicators may be associated to water pollution and belong to the group of environmental footprint indicators.

The calculation of the COD indicator may be based on primary data to be filled by the user. The primary data may include information about the site's discharge. In the case where the wastewater is discharged into the municipal sewer system, a removal rate may be applied. In examples, the removal rate may be 82%.

The calculation of the freshwater ecotoxicity indicator may be based on data, including primary data, which may include site discharge data and is completed by the user, and other data such characterization factors for different substances. If the wastewater is discharged in the municipal sewage system, a removal rate is applied. In examples, the removal rate may be specific to each substance.

In examples, the indirect impact of energy and/or chemicals is also taken into account when calculating the COD indicator and the freshwater ecotoxicity indicator. indirect impact is calculated by converting data using a database. In examples, the database may be ecoinvent 3.3.

Indicators Associated with Water Risk Assessment.

The computation of a water risk assessment indicator may comprise calculating the mathematical product of a cost value and a probability. The higher the value of the mathematical product, the higher the risk. The cost value represents the importance of the water for the site. In examples, the probability may be the product of an internal factor and an external factor. In examples the internal factor may result from a weighted average of several internal factors and the external factor may result from a weighted average of several external factors. In examples, the calculation of water-related risk indicators can be based on the GEMI Local Water Tool—IPIECA.

A physical indicator of water stress and/or a physical indicator of water quality may be automatically calculated. The physical indicator of water stress measures the importance of water for the site and the probability that it will be under water stress (e.g. lack of water). The physical water quality indicator measures the importance for the site to discharge its water and the risk to impact the receiving body and thus to be forbidden to discharge.

In examples, the internal factors used when calculating the physical water stress indicator may include one or more values representing the amount of water withdrawn per type of resource and/or engagement with local water authorities to secure water supply. External factors may include one or more values representing the availability of the resource, the quality of the resource, the generic water stress index drought pattern and/or demand increase.

In examples, the internal factors used when calculating the physical water quality indicator may include a value representing water pollution footprint (COD or ecotoxicity). External factors may include a value representing the capacity of the body of water to absorb water pollution.

Figure 7:
FIG. 7 shows an example of a TRL scale.

In addition, one or more indicators of regulatory risks, reputation and/or level of technological readiness can also be calculated. The technology readiness indicator quantifies a risk related to the maturity of the site's technology. The technology readiness indicator can be calculated based on the TRL framework. FIG. 7 shows an example of a TRL scale.

In examples, when calculating a regulatory risk indicator, internal and/or external factors may include values representing current regulatory issues and/or potential future regulatory issues.

In examples, when calculating a reputational risk indicator, internal and/or external factors may include values representing issues related to the company's local reputation and/or an effect on local activism.

Indicators Associated with Social Impact.

In examples, indicators associated with social impact can quantify the impact of the scenario in terms of employment, local acceptance and/or burdens for the local population.

In examples, an employment indicator can quantify a number of jobs directly and/or indirectly supported by the scenario. In addition or alternatively, an employment indicator can provide data on the stability of the jobs involved in the scenario.

In the examples, a local acceptance indicator may indicate the acceptability of the water use scenario by the local population.

In examples, one or more load indicators for the local population can quantify the effect of noise, odors and/or release of hazardous substances on the local population.

Exampled of the method according to the first aspect have been discussed. Those skilled in the art will appreciate that the provided discussions also apply to the method according to the second aspect. In particular, examples of the method according to the second aspect may implement discussed indicators, discussed collected data, discussed GUIs, and/or discussed steps.

The invention claimed is:

1. A computer-implemented method of water management for an industrial site, the method comprising:
   collecting, via user-interaction, data related to one or more exploitation scenarios of the industrial site, the one or more exploitation scenarios comprising a first exploitation scenario and a second exploitation scenario;
   for each respective exploitation scenario:
      computing, automatically by a computer system and based on the collected data, for each indicator of a plurality of indicators, a respective indicator value, the plurality of indicators comprising:
         a first group of one or more water risk assessment indicators including:
            a physical water stress indicator, and/or
            a physical water quality indicator, and
         a second group of one or more environmental footprint indicators including:
            a carbon footprint indicator,
            a freshwater withdrawal indicator,
            a water scarcity footprint indicator,
            a COD indicator,
            a freshwater ecotoxicity indicator,
            a water withdrawal indicator, and/or
            a freshwater consumption indicator,
      displaying, simultaneously on a display of the computer system, a plurality of graphical representations including:
         for the indicator value of each indicator of the first group, a respective graphical representation, and
         for the indicator value of each indicator of the second group, a respective graphical representation, the plurality of graphical representations including graphical representations respective to the first scenario and graphical representations respective to the second scenario being displayed simultaneously and superposed.

2. The method of claim 1, wherein:
the first group includes:
the physical water stress indicator, and
the physical water quality indicator, and
the second group includes:
the carbon footprint indicator,
the freshwater withdrawal indicator,
the water scarcity footprint indicator,
the COD indicator, and
the freshwater ecotoxicity indicator.

3. The method of claim 2, wherein the second group further includes the water withdrawal indicator and/or the freshwater consumption indicator.

4. The method of claim 1 further comprising, after the displaying, exploiting the industrial site based on the displaying and as a function of at least one of the one or more exploitation scenarios.

5. The method of claim 1, wherein the graphical representations respective to the first scenario and the graphical representations respective to the second scenario, which are displayed superposed, are displayed superposed on a radar chart.

6. The method of claim 5, wherein the radar chart comprises a first polyline in a first color and representing indicator values of the first scenario and a second polyline in a second color and representing indicator values of the second scenario, the first color and the second color being different.

7. The method of claim 5 wherein the radar chart is partitioned into a plurality of domains, wherein each domain delimits a respective range of values for each indicator represented in the radar chart.

8. The method of claim 5 wherein the displaying comprises a display of the radar chart adjacent to at least one histogram chart, wherein each histogram chart represents at least one parameter associated with a respective indicator represented in the radar chart.

9. The method of claim 1 wherein for the indicator value of one or more indicators of the first group and/or one or more indicators of the second group, a given respective graphical representation respective to the first scenario and a given respective graphical representation respective to the second scenario are displayed in a same respective chart.

10. The method of claim 4 wherein the first exploitation scenario and/or the second exploitation scenario include a water recycling process.

11. The method of claim 1 wherein the collected data related to at least one exploitation scenario comprise data representing a set of on-site processes, the computing including, for at least one indicator value, calculating a respective direct impact of the set of on-site processes and a respective indirect impact of the set of on-site processes.

12. The method of claim 11, wherein the data representing the set of on-site processes comprise on-site energy consumption data, on-site water flowrate balance data, on-site waste data, on-site chemical consumption, and/or composition of waste water.

13. The method of claim 12, wherein the on-site waste data include effluent data.

14. The method of claim 13, wherein the industrial site is an oil and/or gas industrial site, and the effluent data comprise one or more polycyclic aromatic hydrocarbons, one or more BTEX, one or more phenols, and/or one or more metals.

15. The method of claim 11 wherein:
the plurality of graphical representations includes, for the at least one indicator value, a respective graphical representation which differentiates the respective direct impact and the respective indirect impact;
the collected data further comprise geographical data, the calculating of the respective indirect impact being based on the geographical data; and/or
the computing includes accessing a conversion database, the calculating of the indirect impact being based on the conversion database.

16. A computer program product comprising:
a computer-readable storage medium embodying code instructions that, when executed by a computer system, cause the computer system to perform water management of an industrial site by:
collecting, via user-interaction, data related to one or more exploitation scenarios of the industrial site, the one or more exploitation scenarios comprising a first exploitation scenario and a second exploitation scenario; and
for each respective exploitation scenario:
computing, automatically by the computer system and based on the collected data, for each indicator of a plurality of indicators, a respective indicator value, the plurality of indicators comprising:
a first group of one or more water risk assessment indicators including any one or combination of:
a physical water stress indicator, and
a physical water quality indicator, and
a second group of one or more environmental footprint indicators including any one or combination of:
a carbon footprint indicator,
a freshwater withdrawal indicator,
a water scarcity footprint indicator,
a COD indicator,
a freshwater ecotoxicity indicator,
a water withdrawal indicator, and
a freshwater consumption indicator, and
displaying, simultaneously on a display of the computer system, a plurality of graphical representations including:
for the indicator value of each indicator of the first group, a respective graphical representation, and
for the indicator value of each indicator of the second group, a respective graphical representation,
the plurality of graphical representations including graphical representations respective to the first scenario and graphical representations respective to the second scenario being displayed simultaneously and superposed.

17. A computer-readable medium comprising:
a memory area having recorded thereon computer program instructions executable by a processor to perform water management for an industrial site by:
collecting, via user-interaction, data related to one or more exploitation scenarios of the industrial site, the one or more exploitation scenarios comprising a first exploitation scenario and a second exploitation scenario; and
for each respective exploitation scenario:

computing, automatically by a computer system and based on the collected data, for each indicator of a plurality of indicators, a respective indicator value, the plurality of indicators comprising:
   a first group of one or more water risk assessment indicators including any one or combination of:
     a physical water stress indicator, and
     a physical water quality indicator, and
   a second group of one or more environmental footprint indicators including any one or combination of:
     a carbon footprint indicator,
     a freshwater withdrawal indicator,
     a water scarcity footprint indicator,
     a COD indicator,
     a freshwater ecotoxicity indicator,
     a water withdrawal indicator, and
     a freshwater consumption indicator, and
displaying, simultaneously on a display of the computer system, a plurality of graphical representations including:
   for the indicator value of each indicator of the first group, a respective graphical representation, and
   for the indicator value of each indicator of the second group, a respective graphical representation,
   the plurality of graphical representations including graphical representations respective to the first scenario and graphical representations respective to the second scenario being displayed simultaneously and superposed.

18. A computer system comprising:
a processor coupled to a memory,
the memory having recorded thereon instructions executable by the processor to perform water management of an industrial site including instructions to:
collect, via user-interaction, data related to one or more exploitation scenarios of the industrial site, the one or more exploitation scenarios comprising a first exploitation scenario and a second exploitation scenario; and
for each respective exploitation scenario:
   compute, automatically by the computer system and based on the collected data, for each indicator of a plurality of indicators, a respective indicator value, the plurality of indicators comprising:
     a first group of one or more water risk assessment indicators including:
       a physical water stress indicator, and/or
       a physical water quality indicator, and
     a second group of one or more environmental footprint indicators including:
       a carbon footprint indicator,
       a freshwater withdrawal indicator,
       a water scarcity footprint indicator,
       a COD indicator,
       a freshwater ecotoxicity indicator,
       a water withdrawal indicator, and/or
       a freshwater consumption indicator, and
   display, simultaneously on a display of the computer system, a plurality of graphical representations including:
     for the indicator value of each indicator of the first group, a respective graphical representation, and
     for the indicator value of each indicator of the second group, a respective graphical representation,
     the plurality of graphical representations including graphical representations respective to the first scenario and graphical representations respective to the second scenario being displayed simultaneously and superposed.

\* \* \* \* \*